(12) United States Patent
Chu et al.

(10) Patent No.: US 9,353,037 B2
(45) Date of Patent: May 31, 2016

(54) GRAPHENE OXIDE-BASED COMPOSITE MEMBRANES

(71) Applicant: The Research Foundation of State University of New York, Albany, NY (US)

(72) Inventors: Benjamin Chu, Setauket, NY (US); Benjamin S. Hsiao, Setauket, NY (US); Devinder Mahajan, South Setauket, NY (US); Tsung-Ming Yeh, Port Jefferson Station, NY (US)

(73) Assignee: The Research Foundation For The State University of New York, Albany, NY (US)

( * ) Notice: Subject to any disclaimer, the term of this patent is extended or adjusted under 35 U.S.C. 154(b) by 36 days.

(21) Appl. No.: 14/083,568

(22) Filed: Nov. 19, 2013

(65) Prior Publication Data
US 2015/0141711 A1    May 21, 2015

(51) Int. Cl.
| | | |
|---|---|---|
| *B01D 39/00* | (2006.01) | |
| *B01D 29/46* | (2006.01) | |
| *B01D 15/00* | (2006.01) | |
| *C02F 1/44* | (2006.01) | |
| *C07C 29/76* | (2006.01) | |
| *B01D 71/10* | (2006.01) | |
| *B01D 71/42* | (2006.01) | |
| *B01D 71/48* | (2006.01) | |
| *B01D 69/10* | (2006.01) | |
| *B01D 69/12* | (2006.01) | |
| *B01D 71/02* | (2006.01) | |
| *B01D 61/36* | (2006.01) | |

(52) U.S. Cl.
CPC .............. *C07C 29/76* (2013.01); *B01D 69/10* (2013.01); *B01D 69/12* (2013.01); *B01D 71/024* (2013.01); *B01D 71/028* (2013.01); *B01D 71/10* (2013.01); *B01D 71/42* (2013.01); *B01D 71/48* (2013.01); *B01D 61/362* (2013.01); *B01D 2323/39* (2013.01); *Y02P 20/57* (2015.11); *Y02P 20/572* (2015.11)

(58) Field of Classification Search
CPC ........ B82Y 30/00; B82Y 40/00; A61K 33/42; A61L 2400/12; A61L 27/422; C01B 2204/30; Y10S 977/734; Y10S 977/742; Y10S 977/746
See application file for complete search history.

(56) References Cited

U.S. PATENT DOCUMENTS

| | | | |
|---|---|---|---|
| 2,882,243 | A | 4/1959 | Milton |
| 5,230,801 | A | 7/1993 | Darnell et al. |
| 5,288,712 | A | 2/1994 | Chen |
| 5,556,539 | A | 9/1996 | Mita et al. |
| 6,755,975 | B2 | 6/2004 | Vane et al. |
| 8,054,323 | B2 * | 11/2011 | Peters et al. ................ 347/221 |

(Continued)

OTHER PUBLICATIONS

R.R. Nair, et al., "Unimpeded Permeation of Water Through Helium-Leak-Tight Graphene-Based Membranes", Science, vol. 335, pp. 442-444 (2012).

(Continued)

*Primary Examiner* — Ana Fortuna
(74) *Attorney, Agent, or Firm* — Carter, DeLuca, Farrell & Schmidt, LLP

(57) ABSTRACT

Membranes are provided for energy efficient purification of alcohol by pervaporation. Such membranes include a nanofibrous scaffold in combination with a barrier layer. The barrier layer includes a graphene oxide. The membranes may, in embodiments, also include a substrate.

20 Claims, 2 Drawing Sheets

(56) References Cited

U.S. PATENT DOCUMENTS

| | | | |
|---|---|---|---|
| 8,231,013 B2* | 7/2012 | Chu et al. | 210/500.1 |
| 8,278,643 B2* | 10/2012 | Bowers et al. | 257/9 |
| 8,703,090 B2* | 4/2014 | Tour et al. | 423/447.1 |
| 8,911,996 B2* | 12/2014 | Srouji et al. | 435/398 |
| 8,940,092 B1* | 1/2015 | Yeo et al. | 117/68 |
| 8,979,978 B2* | 3/2015 | Miller et al. | 95/47 |
| 9,005,607 B2* | 4/2015 | Kumar et al. | 424/93.7 |
| 9,017,474 B2* | 4/2015 | Geim et al. | 106/287.28 |
| 2011/0017390 A1* | 1/2011 | Blake et al. | 156/247 |
| 2011/0201201 A1* | 8/2011 | Arnold et al. | 438/694 |
| 2011/0240947 A1* | 10/2011 | Yang et al. | 257/3 |
| 2014/0305864 A1* | 10/2014 | Sun et al. | 210/505 |
| 2014/0328373 A1* | 11/2014 | Panda | G01K 1/143 374/163 |
| 2014/0370246 A1* | 12/2014 | Hurt | 428/189 |
| 2015/0108872 A1* | 4/2015 | Pinkerton | B81B 3/00 310/300 |
| 2015/0141711 A1* | 5/2015 | Chu et al. | 568/918 |
| 2015/0174532 A1* | 6/2015 | Wilson | |
| 2015/0183189 A1* | 7/2015 | Kim et al. | |
| 2015/0298976 A1* | 10/2015 | Lee | B82Y 40/00 428/702 |

OTHER PUBLICATIONS

Hummers, et al., "Preparation of Graphitic Oxide", J Am. Chem. Soc., vol. 80, p. 1339 (1958).

Yeh, et al., "Polymeric nanofibrous composite membranes for energy efficient ethanol dehydration", Journal of Renewable and Sustainable Energy, vol. 4, pp. 041406-1-041406-9 (2012).

Eda, et al., "Chemically Derived Graphene Oxide: Towards Large-Area Thin-Film Electronics and Optoelectronics", Advanced Materials, vol. 22, pp. 2392-2415 (2010).

Putz, et al., "High-Nanofiller-Content Graphene Oxide-Polymer Nanocomposites via Vacuum-Assisted Self-Assembly", Advanced Functional Materials, vol. 20, pp. 3322-3329 (2010).

Dikin, et al., "Preparation and characterization of graphene oxide paper", Nature, vol. 448, pp. 457-460 (2007).

\* cited by examiner

GRAPHENE OXIDE-BASED COMPOSITE MEMBRANES

GOVERNMENT RIGHTS

This invention was made with Government Support under grant numbers IIP0832520 and DMRI019370 awarded by the National Science Foundation. The government has certain rights in the invention.

BACKGROUND

Applications of electrospun nanofibrous membranes for liquid filtration have recently been demonstrated for microfiltration, ultrafiltration and nanofiltration. These membranes can effectively increase the permeability of a membrane formed therefrom, while maintaining high rejection ratios.

Biofuels are a wide range of fuels derived from biomass. Two of the more utilized biofuels include ethanol derived from corn grain and biodiesel derived from soybeans. There has been a steady increase in demand for biofuels, especially with the use of ethanol as an additive to gasoline in the U.S.

Industrial alcohol can be obtained from fermentation of suitable biomass (e.g. corn) using multi-staged distillation processes, which are based on the different boiling points between water, ethanol and their mixtures When ethanol is added into gasoline, its water content must be minimized because gasoline/ethanol mixture should not contain water. In other words, for most industrial and fuel applications, ethanol must be purified to minimize the water content. The final dehydration step in alcohol purification process usually requires a great deal of energy and is expensive to complete. There are also issues with exhaust/emissions. Currently, the distillation method is the most widely adopted, but it requires high energy consumption.

Membranes and methods permitting more energy efficient purification of alcohol remain desirable.

SUMMARY

The present disclosure provides pervaporation membranes (PV membranes) that include a combination of an electrospun nanofibrous scaffold and a graphene oxide barrier layer. The membrane may be produced by casting a graphene oxide (GO) barrier layer on the scaffold. The resulting membranes exhibit simultaneous improvements in permeation flux and separation factor in pervaporation applications, including ethanol dehydration.

In embodiments, the present disclosure provides an article including a nanofibrous scaffold possessing fibers having a diameter of from about 1 nm to about 20,000 nm; and a barrier layer including graphene oxide on at least a portion of a surface of the nanofibrous scaffold, wherein the barrier layer has a thickness from about 5 nm to about 5000 nm.

In other embodiments, an article of the present disclosure includes a substrate; a nanofibrous scaffold possessing fibers having a diameter of from about 1 nm to about 20,000 nm applied to a surface of the substrate; and a barrier layer including graphene oxide on the nanofibrous scaffold on a surface opposite the surface applied to the substrate, wherein the barrier layer has a thickness from about 5 nm to about 5000 nm.

Methods for producing the pervaporation membranes are also provided, as are methods for their use in purifying alcohol by pervaporation.

BRIEF DESCRIPTION OF THE FIGURES

Various embodiments of the present disclosure will be described herein with reference to the following figures, wherein.

DETAILED DESCRIPTION

Figure 1:
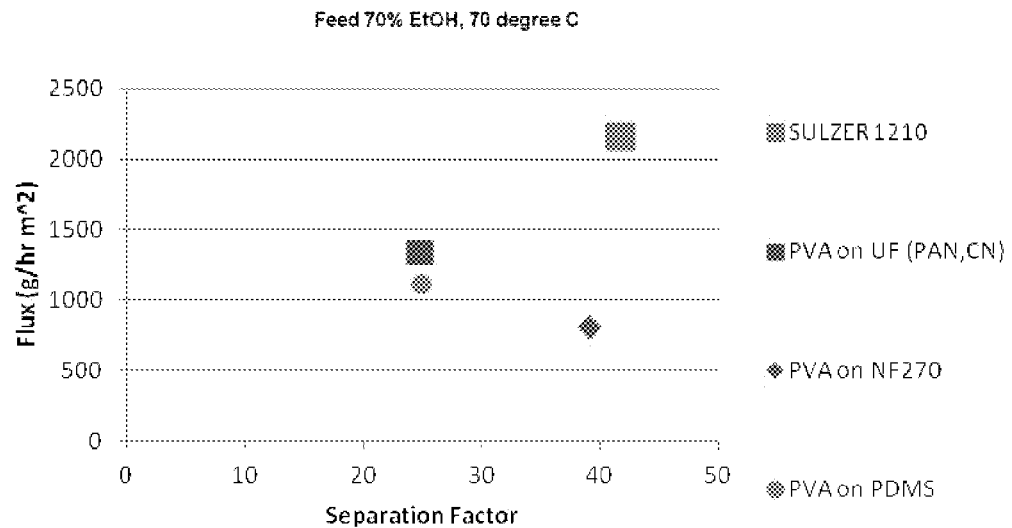
FIG. 1 is a graph comparing pervaporation performance of membranes with the same PVA barrier layer, but different scaffolds.

As an alternative to distillation procedures, in accordance with the present disclosure, pervaporation is utilized to produce fuel grade ethanol with very low energy consumption. Pervaporation combines both permeation and evaporation to enhance the removal of water from ethanol, i.e., the dehydration of ethanol.

Pervaporation systems vary and are within the purview of those skilled in the art. Generally speaking, a pervaporation system includes, at a minimum, a supply line/feed pump, a membrane module, a withdrawal line/vacuum pump, and a condenser. Generally, a vacuum or an inert sweep gas, such as $N_2$, is applied on the permeate side of the membrane to maintain a partial pressure difference across the membrane, which facilitates volatilization of permeates for subsequent condensation and recovery.

Suitable pervaporation systems include those disclosed in U.S. Pat. Nos. 5,230,801, 5,288,712, 5,556,539, and 6,755,975, the entire disclosures of each of which are incorporated by reference herein.

The present disclosure provides a novel pervaporation membrane (PV membrane), based on the combination of an electrospun nanofibrous scaffold and a graphene oxide barrier layer. The PV membranes of the present disclosure may be utilized with any system capable of carrying out pervaporation. In embodiments, the PV membranes of the present disclosure may be used for alcohol, such as ethanol, purification.

The membranes of the present disclosure include a composite structure with multiple layers. One layer includes a non-woven nanofibrous scaffold. In some embodiments, the scaffold layer includes electrospun nanofibers. A second layer is a graphene oxide barrier layer. In accordance with the present disclosure nanofibrous membranes are enhanced for pervaporation applications, such as the separation of water and ethanol.

Electrospun nanofibrous scaffolds have high porosity (up to about 80% and, in some cases, greater than about 80%), high surface to volume ratio of the material from about 4 $\mu m^{-1}$ to about 40 $\mu m^{-1}$ in embodiments from about 8 $\mu m^{-1}$ to about 20 $\mu m^{-1}$ in embodiments very high specific surface area due to fine nanofibers (having diameters from about 0.1 µm to about 1 µm, in embodiments from about 0.2 µm to about 0.8 µm), and interconnected-pore structures. Electrospun nanofibrous scaffolds can be used as a supporting layer in forming thin-film nanofibrous composite (TFNC) ultra-filtration and nano-filtration membranes. These membranes possess very high permeation flux from about 20 $L/m^2h$ to about 600

$L/m^2h$, in embodiments from about 100 $L/m^2h$ to about 500 $L/m^2h$ increased by a factor of from about 2 to about 10 when compared with typically commercial membranes), and a high rejection rate, in embodiments from about 80% to about 99%, in other embodiments from about 85% to about 95%.

These scaffolds may be made of suitable polymers within the purview of one skilled in the art, including, but not limited to, polyolefins including polyethylene and polypropylene, polysulfones such as polyethersulfone, fluoropolymers such as polyvinylidene fluoride, polyesters including polyethylene terephthalate, polytrimethylene terephthalate, and polybutylene terephthalate, polyamides including nylon 6, nylon 66, and nylon 12, polycarbonates, polystyrenes, polynitriles such as polyacrylonitrile, polyacrylates such as polymethyl methacrylate, polyacetates such as polyvinyl acetate, polyalcohols such as polyvinyl alcohol, polysaccharides (such as chitosan, cellulose, collagen, or gelatin), proteins such as chitin, hyaluronic acid, polyalkylene oxides such as polyethylene oxide and polyethylene glycol, polyurethanes, polyureas, polyvinyl chloride, polyimines such as polyethylene imine, polyvinylpyrrolidone, polyacrylic acids, polymethacrylic acids, polysiloxanes such as polydimethylsiloxane, poly(ester-co-glycol) copolymers, poly(ether-co-amide) copolymers, crosslinked forms thereof, derivatives thereof and copolymers thereof. In some embodiments, poly(acrylonitrile) (PAN), polyethersulfone (PES), polyvinylidenefluoride (PVDF), crosslinked water soluble polymers, e.g., polyvinylalcohol (PVA), modified cellulose and modified chitosan, their chemical derivatives and/or copolymers, may be utilized. Combinations of the foregoing may also be used to form suitable scaffolds.

In some embodiments, it may be desirable to crosslink fluid-soluble polymers to form a nanofibrous scaffold. For example, water-soluble polymers, such as polyvinyl alcohol, polysaccharides (including chitosan and hyaluronan), polyalkylene oxides (including polyethylene oxide), gelatin, and their derivatives may be crosslinked to render these polymers suitable for use as a hydrophilic nanofibrous scaffold. Crosslinking may be conducted using methods within the purview of those skilled in the art, including the use of crosslinking agents. Suitable crosslinking agents include, but are not limited to, $C_2$-$C_8$ dialdehyde, $C_2$-$C_8$ diepoxy, $C_2$-$C_8$ monoaldehydes having an acid functionality, $C_2$-$C_9$ polycarboxylic acids, combinations thereof, and the like. These compounds are capable of reacting with at least two hydroxyl groups of a water-soluble polymer.

Other suitable crosslinking methods include conventional thermal-, radiation- and photo-crosslinking reactions within the purview of those skilled in the art. Two important criteria for the selection of a crosslinking agent or method are as follows: (1) the crosslinking agent or method should not dissolve the nanofibrous scaffold layer, and (2) the crosslinking agent or method should not induce large dimensional change, e.g., hydrophilic electrospun nanofibrous scaffold layers may display very large shrinkage in hydrophobic solvents such as hydrocarbons because of their hydrophilic nature.

Specific examples of crosslinking agents which may be utilized include, but are not limited to, glutaraldehyde, 1,4-butanediol diglycidyl ether, glyoxal, formaldehyde, glyoxylic acid, oxydisuccinic acid, citric acid, fumaric acid, combinations thereof, and the like. In some embodiments, it may be useful to treat polyvinyl alcohol with a crosslinking agent such as glutaraldehyde.

The amount of crosslinking agent added to the water-soluble polymer, such as polyvinyl alcohol, may vary from about 0.1 to about 10 percent by weight of the combined weight of the crosslinking agent and polymer, in embodiments from about 0.5 to about 5 percent by weight of the combined weight of the crosslinking agent and polymer.

The thickness of the nanofibrous scaffold may vary from about 1 µm to about 500 µm, in embodiments from about 10 µm to about 300 µm, in embodiments from about 30 µm to about 150 µm in thickness. In some embodiments, the thickness of the scaffold is from about 40 µm to about 50 µm.

The nanofibrous scaffold possesses pores or voids which assist in the functioning of the membranes of the present disclosure. The diameter of these voids may be from about 10 nm to about 200 µm, in embodiments from about 50 nm to about 30 µm, in embodiments from about 100 nm to about 10 µm. In some embodiments, the pore size may be from about 0.2 µm to about 0.6 µm.

In forming the nanofibrous scaffold of the present disclosure, the polymer is often first placed in a solvent, such as N,N-dimethyl formamide (DMF), tetrahydrofuran (THF), methylene chloride, dioxane, ethanol, propanol, butanol, chloroform, water, or combinations of these solvents, so that the polymer is present at an amount from about 1 to about 40 percent by weight of the polymer solution, in embodiments from about 3 to about 25 percent by weight of the polymer solution, in embodiments from about 5 to about 15 percent by weight of the polymer solution.

In some embodiments, it may be desirable to add a surfactant or another solvent-miscible liquid to the polymer solution utilized to form the nanofibrous scaffold. The surfactant or other solvent-miscible liquid may lower the surface tension of the solution, which may help stabilize the polymer solution during electro-spinning, electro-blowing, and the like. Suitable surfactants include, for example, octylphenoxypolyethoxy ethanol (commercially available as TRITON X-100), sorbitan monolaurate, sorbitan sesquioleate, glycerol monostearate, polyoxyethylene, polyoxyethylene cetyl ether, dimethyl alkyl amines, methyl dialkyl amines, combinations thereof, and the like. Where utilized, the surfactant may be present in an amount from about 0.001 to about 10 percent by weight of the polymer solution, in embodiments from about 0.05 to about 5 percent by weight of the polymer solution, in embodiments from about 0.1 to about 2 percent by weight of the polymer solution. The solvent miscible fluid with the solvent forms a solvent mixture that can dissolve the polymer but changes the surface tension of the polymer solution and the evaporation rate of the solvent mixture.

In embodiments, the nanofibrous scaffold may be fabricated using electro-spinning, electro-blowing, blowing-assisted electro-spinning, and/or solution blowing technologies. Electro-spinning processes use mainly electric force, but often without the assistance of gas flow. To the contrary, solution blowing processes use only gas flow, without the use of electric force. Blowing-assisted electro-spinning and electro-blowing both use electric force and gas-blowing shear forces. In blowing-assisted electro-spinning processes, the electric force is the dominating factor, while the gas-blowing feature can assist in shearing the fluid jet stream and in controlling the evaporation of the solvent (lower throughput, smaller diameter). In contrast, in electro-blowing processes the gas-blowing force is the dominating factor to achieve the desired spin-draw ratio, while the electric force may enable further elongation of fibers (higher throughput, larger diameter).

In embodiments, a membrane of the present disclosure may include a graphene oxide (GO) barrier layer on a supporting scaffold. Other thin sheet materials, such as exfoliated clays or a combination of materials having small channels, such as zeolites, may also be used as the barrier layer.

Graphene is a single layer of carbon atoms with many useful properties. Graphene may be obtained from graphite by mechanical exfoliation, by epitaxial growth, and reduction of either silicon carbide or graphene oxide. Graphene oxide (GO) is an electrically insulating material composed of a single graphene sheet with oxygen functional groups bonded to the graphene basal-plane. Graphene oxide (GO) can be obtained from the exfoliation of graphite oxide. Similar to graphene, GO also possesses one-atom thick sheets with high surface-to-volume ratio and extraordinary physical properties. In addition, GO can form a stable aqueous suspension due to the presence of carboxyl groups and hydroxyl groups on the edge or the side of GO sheets.

Due to oxygen functional groups such as carboxyls, epoxides, and alcohols, GO is hydrophilic and can readily exfoliate as single sheets when ultrasonicated in $H_2O$. The average size of an individual GO sheet, dispersed in $H_2O$, may be about 1 $\mu m^2$, with a thickness of from about 1 to about 1.5 nm.

GO membranes, having a layer thickness in the submicron range, allow unimpeded permeation of water vapor, but are totally impermeable to other liquid and gas molecules, including helium. This unique behavior may be attributed to the phenomenon of "nanocapillaries" formed between the flakes of GO that make up the GO sheets. In other words, the hydrophilic nature of carboxylic acid groups and hydroxyl groups (which attracts water molecules) may create the tortuous network of confined water channels, allowing the transport of water molecules but preventing the diffusion of larger size and hydrophobic molecules.

Methods for producing graphene oxide, as noted above, are within the purview of those skilled in the art. Graphene oxide is also commercially available, for example, from Graphene Supermarket, Inc. (Calverton, N.Y.).

Graphene oxide may be applied to a supporting scaffold utilizing methods within the purview of those skilled in the art. In embodiments, graphene oxide may be in a solution, which may then be applied to the supporting scaffold by dipping, spraying, casting, spin coating, vacuum filtration, chemical vapor deposition (CVD), the Langmuir-Blodgett method, combinations thereof, and the like.

Suitable solvents for forming the graphene oxide solution include, for example, water, ethylene glycol, dimethylformamide (DMF), n-methylpyrrolidone (NMP), tetrahydrofuran (THF), combinations thereof, and the like. The graphene oxide may be present in the solution in amounts from about $1 \times 10^{-10}$% by weight of the solution to about 10% by weight of the solution, depending on the mean size of exfoliated graphene oxide sheets, in embodiments from about $5 \times 10^{-8}$% by weight of the solution to about 0.5% by weight of the solution.

The resulting layer of graphene oxide may have a thickness from about 5 nm to about 5000 nm, in embodiments from about 50 nm to about 2000 nm, in embodiments from about 100 nm to about 1000 nm. The resulting membrane may have a permeate flux of from about $1 \times 10^{-6}$ $kg/m^2$ hr to about 10 $kg/m^2$ hr, in embodiments from about 0.1 $kg/m^2$ hr to about 2.5 $kg/m^2$ hr. The resulting membrane may have a separation factor from about $1 \times 10^{-2}$ to about $1 \times 10^4$, in embodiments from about 100 to about 1000.

In embodiments, the nanofibrous scaffold and/or the graphene oxide barrier layer may contain zeolites and additional organic/inorganic components. Such components may be added using methods within the purview of those skilled in the art, including the addition of a polymer as an annealing agent. Zeolites are solid adsorbents, sometimes referred to as molecular sieves. Zeolites are microporous crystalline solids with well-defined structures. Generally they contain silicon, aluminium and oxygen in their framework, and cations, water and/or other molecules within their pores. Many occur naturally as minerals, and are extensively mined in many parts of the world. Others are synthetic, and are made commercially for specific uses, including use as ion exchange materials, catalysts, and/or adsorbents.

As noted above, zeolites generally include a substitution of aluminum for silicon in their framework, which creates a charge imbalance that requires a non-framework cation to balance the charge. In embodiments, sodium may be included as a cation. These cations, which are contained inside the pores of these materials, may be replaced by other cations giving rise to ion-exchange properties.

Zeolites suitable for use according to the present disclosure include any known varieties, for example types A, X, P, Y, natural zeolites, and combinations thereof. The types are distinguished based upon, among other things, elements making up the zeolite, its channel/pore system, and its framework. For example, the synthesis of zeolite A is described in U.S. Pat. No. 2,882,243.

Suitable zeolites possess a significant level of crystallinity. In some embodiments, the zeolite has a mean micropore diameter from about 2.8 Angstroms to about 8 Angstroms, in embodiments from about 3 Angstroms to about 5 Angstroms, and/or an external surface area of from about 3 $m^2/g$ to about 300 $m^2/g$, in embodiments from about 100 $m^2/g$ to about 250 $m^2/g$.

Examples of suitable zeolites include those commercially available under the trade names VALFOR 100 and ADVERA 401PS, both available from PQ Corporation of Valley Forge, Pa. Also useful are zeolites in which some or all of the sodium ions have been replaced by potassium and/or calcium ions, for example zeolites 3A and 5A. Other nonlimiting examples of suitable potential ion-exchange cations include Ag, Zn, and Cu, with replacement of sodium by these cations being partial or complete.

In embodiments, the zeolite may be present in amounts from about 0.1% by weight to about 50% by weight of the scaffold, in embodiments from about 1% by weight to about 10% by weight of the scaffold.

In embodiments, in addition to the nanofibrous scaffold and GO barrier layer described above, membranes of the present disclosure may also include any substrate currently in use with filtration membranes.

Such substrates include, but are not limited to, hydrophilic polymers, hydrophobic polymers, hydrophilic/hydrophobic copolymers, polyelectrolytes, and ion-containing polymers. Specific examples of polymers which may be utilized include, but are not limited to, polyolefins including polyethylene and polypropylene, polyesters including polyethylene terephthalate, polytrimethylene terephthalate and polybutylene terephthalate, polyamides including nylon 6, nylon 66, and nylon 12, polyurethanes, fluorinated polymers, polyetherketones, polystyrene, sulfonated polyetherketones, sulfonated polystyrene and derivatives thereof, cellulose and derivatives thereof, and copolymers thereof. In some embodiments, commercially available non-woven substrates made of polyethylene terephthalate (PET), propylene, including isotactic polypropylene (iPP), polyethylene (PE), glass, cellulose and cellulose-based polymers, and fluorinated polymers, may be used as the substrate.

In some embodiments, suitable substrates may include hydrophobic/hydrophilic copolymers. Such copolymers include, but are not limited to, polyurethane copolymers, polyurea copolymers, polyether-b-polyamide, PEG modified fluorinated copolymers, ethylene-propylene copolymers, cellulose based copolymers, ethylene based copolymers, propylene based copolymers, combinations thereof, and the like. These copolymers, which possess excellent mechanical strength and durability, may be useful where such characteristics are desired for the membrane.

Other suitable substrates may be porous membranes, including those fabricated by a phase inversion method. Phase inversion methods are within the purview of those skilled in the art and generally include: (1) casting a solution or mixture possessing high molecular weight polymer(s), solvent(s), and nonsolvent(s) into thin films, tubes, or hollow fibers; and (2) precipitating the polymer. The polymer may be precipitated, in embodiments, by: evaporating the solvent and nonsolvent (dry process); exposing the material to a nonsolvent vapor (e.g. water vapor), which absorbs on the exposed surface (vapor phase-induced precipitation process); quenching in a nonsolvent liquid, generally water (wet process); or thermally quenching a hot film so that the solubility of the polymer is greatly reduced (thermal process).

Suitable porous substrates, including those prepared by phase inversion processes, are within the purview of those skilled in the art and include, for example, substrates produced from polymers such as polysulfones (e.g. polyethersulfone), cellulose acetates, fluoropolymers (e.g. polyvinylidene fluoride (PVDF) and polyoxyethylene methacrylate (POEM) grafted PVDF), polyamides (e.g. poly-ether-b-polyamide), and polyimides. Such substrates may have a pore size of from about 5 nm to about 500 nm, in embodiments, from about 20 nm to about 100 nm.

In some embodiments, the substrate may be assymetrical, having varying pore sizes throughout the substrate. This asymmetry may enhance performance of a membrane utilized for pervaporation. For example, increasing porosity and/or pore diameter may enhance the mass transfer coefficient and pressure losses of a pervaporation membrane formed from such a substrate.

In some embodiments, non-woven poly(ethylene terephthalate) (PET) micro membranes (commercially available as AWA16-1 from SANKO LIMITED, 1316-1 Kawamuko cho, Tsuzuki-ku, Yokohama, 224-0044 Japan, with an average fiber diameter of about 20 μm) can be used as the substrate. In other embodiments, non-woven PET micro filters (commercially available as NOVATEXX 2413 from Freudenberg Filtration Technologies KG, D-69465 Weinheim, Germany), with an average fiber diameter of 20 μm, can be used as the substrate.

As noted above, in embodiments the substrate may be used with a nanofibrous scaffold, sometimes referred to herein as a nanofibrous membrane.

In embodiments, the scaffold layer of the membrane, such as polyacrylonitrile (PAN) or polyethersulfone (PES), may be electrospun on a substrate, such as a non-woven polyethylene terephthalate (PET) micro-filter (AWA16-1 from SANKO LIMITED, 1316-1 Kawamuko cho, Tsuzuki-ku, Yokohama, 224-0044 Japan), utilizing methods within the purview of those skilled in the art.

Where a membrane of the present disclosure possesses multiple layers, the substrate may be used to form a bottom layer having a thickness from about 1 μm to about 300 μm, in embodiments from about 10 μm to about 200 μm, in embodiments from about 50 μm to about 150 μm in thickness; the electrospun nanofibers may form a middle layer having a thickness from about 1 μm to about 100 μm, in embodiments from about 5 μm to about 75 μm, in embodiments from about 30 μm to about 50 μm in thickness; and the top graphene oxide layer may have a thickness from about 5 nm to about 5000 nm, in embodiments from about 50 nm to about 2000 nm, in embodiments from about 100 nm to about 1000 nm in thickness. In other words, a membrane of the present disclosure may include a substrate, a nanofibrous scaffold applied to a surface of the substrate, and a barrier layer including graphene oxide applied to a surface of the nanofibrous scaffold opposite the surface of the nanofibrous scaffold in contact with the substrate. In embodiments, these multi-layer membranes may be referred to as mixed matrix membranes ("MMM").

In embodiments, a general method for preparing membranes in accordance with the present disclosure may include the following. A PAN scaffold or ultrafiltration membrane may be e-spun in water. A casting solution, including graphene oxide, may be prepared and cast onto the PAN scaffold. The materials may then be dried at room temperature and annealed at a suitable temperature, in embodiments about 130° C.

In some embodiments, an additional barrier layer may be placed between the middle nanofibrous layer and the top graphene oxide layer. Such an additional barrier layer provides a smoother, more even surface upon which the hydrophilic barrier layer may be applied, and may prevent the intrusion/penetration of the materials utilized to form the hydrophilic barrier layer into the middle nanofibrous layer. Suitable materials for forming this additional barrier layer include, but are not limited to, cellulose nanofibers, chitin nanofibers, combinations thereof, and the like. The thickness of this additional barrier layer may be from about 0.2 μm to about 2.5 μm, in embodiments from about 0.5 μm to about 1.5 μm, in embodiments from about 0.75 μm to about 1.25 μm in thickness.

Based on the unique TFNC membrane structure, the present disclosure provides a new class of pervaporation membranes that have both a high flux and a high separation factor. In embodiments, these membranes are suitable for use in ethanol dehydration processes.

The advantages of the new class of pervaporation (PV) membranes based on a GO barrier layer and a supporting scaffold are as follows.

(1) The PV membranes' nanocapillaries' within the GO layer can exhibit high flux and high separation performance.
(2) Such GO membranes, after chemical modification, can be used over a wide range of temperatures, from about 10° C. to about 100° C., which matches the operating conditions of industrial ethanol production.
(3) The efficiency of the PV membrane can be further enhanced by reducing the thickness of GO deposition.
(4) The performance of the PV membrane can be tuned by manipulating the morphology of the GO layer, which can be controlled by using established casting methods and changing the surface properties of the GO layer, the dimension of the GO flakes, and the morphology of the flake orientations.
(5) The fabrication of the above PV membranes can be economically scaled up as the casting methods of GO are simple and have been commonly established for mass production.

The following Examples are provided to illustrate, but not limit, the features of the present disclosure so that those skilled in the art may be better able to practice the features of the disclosure described herein.

Comparative Example 1

A hydrophilic barrier layer of cross-linked polyvinyl alcohol (PVA) (having a thickness from about 6 to about 8 microns) was cast on a thin film nanofibrous composite, containing a very thin cellulose nanofiber additional barrier layer, an electrospun mid-layer nanofibrous scaffold (thickness about 40 microns) and a PET non-woven substrate (thickness about 120 microns). For comparison, the same cross-linked polyvinyl alcohol barrier layer was also coated on a nanofiltration membrane (a FILMTEC™ NF270 Membrane, from the Dow Chemical Company) (hereinafter "NF270") as well as on an ultrafiltration membrane made of polydimethylsiloxane (PDMS). The resulting membranes were cut into 3 inch-diameter round disc samples, which were used to evaluate the pervaporation efficiency in ethanol dehydration. In the pervaporation process, 70% ethanol was used as the feeding concentration and the operating temperature was set at 70° C.

The pervaporation performance (i.e., flux versus separation factor) of these three membranes, as well as that of the commercial pervaporation membrane (Sulzer 1210) was calculated, with the results shown in FIG. 1.

The permeation flux was calculated using the following equation:

$$J = Q/A\Delta t \quad (I)$$

where Q=the weight of the permeate collected; A=the effective area of the membrane, and Δt=the time interval for collection.

The separation factor was calculated using the following equation:

$$\alpha = \frac{Y_W/Y_E}{X_W/X_E} \quad (II)$$

where X=the mass fraction in the feed; Y=the mass fractions in the permeate; W=water; and E=ethanol.

As seen in FIG. 1, the membrane based on the electrospun scaffold reached 1.34 (kg/m² hr) for the permeation flux, which was higher than membranes based on the two other scaffolds (PDMS and NF270). The separation factor was about the same for the electrospun scaffold and PDMS, with NF270 being the best. The barrier layer thickness of the three membranes was from about 6 to about 8 microns, several times (from about 6 to about 8 times) thicker than that of the commercial (Sulzer 1210) pervaporation membrane. Thus, the permeation flux of the membrane, normalized by the barrier layer thickness based on the electrospun scaffold, was better than that of the commercial pervaporation membrane (Sulzer 1210).

Example 1

Additional membranes were prepared as described above in Comparative Example 1, with graphene oxide used as the barrier layer. A GO barrier layer was laminated onto the surface of a thin-film nanofibrous composite (TFNC) membrane to fabricate a multilayered pervaporation membrane for ethanol dehydration.

The dispersed GO aqueous solution, in concentration of 5 g/L and flakes of 0.5~5 microns size, were received from Graphene Supermarket, Inc. (Calverton, N.Y.) and subsequently treated with the Hummer method. (See, J. William, S. Hummers, R. E. Offeman, J. Am. Chem. Soc. 80, 1339 (1958).) (Hummers et al. developed a simple oxidation method by reacting graphite with a mixture of potassium permanganate and concentrated sulfuric acid.) Nonwoven polyethylene terephthalate (PET) substrate (Hollytex 3242) was purchased from the Ahlstrom Mount Holly Springs Company. Cellulose raw material in suspension (Biofloc 96 MV, 22% wt. of wood pulp) was supplied by Tembec Tartas Company in France. Sulzer 1210, a PVA composite membrane, was obtained from Sulzer Chemtech. 95 vol. % of ethanol in water was purchased from Sigma Aldrich, Inc.

The chosen scaffold (mat) to support the GO barrier layer was an experimental thin-film nanofibrous composite (TFNC) membrane containing an average pore size of 20 nm in the top layer. This TFNC membrane included three layers: a cellulose ultra-fine nanofibrous top layer, a polyacrylonitrile (PAN) electrospun nanofibrous mid-layer, and a polyethylene terephthalate (PET) nonwoven microfibrous substrate. Practical applications of these TFNC membranes include high-flux microfiltration and ultrafiltration, as well as pervaporation. In general, TFNC membranes exhibit several advantages over conventional polymeric membranes made by the phase inversion method. These advantages include large bulk porosity (80%) and fully interconnected pore structures, which are especially useful to avoid the Knudsen diffusion in gas separation and pervaporation.

A spin coating or vacuum filtration method was used to cast the GO barrier layer on the TFNC membrane. (See, e.g., G. Eda, M. Chhowalla, Adv. Mater. 22, 2392-2415 (2010); R. R. Nair, Wu, H. A, P. N Jayaram, I. V. Grigorieva, A. K Geim, Science, 335, 442-444 (2012); K. W. Putz, O. C. Compton, M. J. Palmeri, S. T. Nguyen, L. C. Brinson, Adv. Func. Mater. 20, 3322-3329 (2010).) By considering the unique flake shape of GO, one way to fabricate GO films is to assemble the GO flakes by gravity. The process for laying down the flakes parallel to the gravitational field is a delicate process which may be accomplished, as noted above, by spin coating or vacuum filtration methods. These methods provided an economical and practical pathway to produce defect-free films on a nanoporous support, when compared with other casting methods such as chemical vapor deposition (CVD) Langmuir-Blodgett assembly, layer-by-layer coating, and evaporation coating.

Water contact angle was determined by using an optical contact angle meter (CAM200, KSV Instruments, LTD). SEM micrographs were obtained using the LEO 1550 instrument equipped with a Schottky field emission gun (20 kV) and a Robinson backscatter detector. The TEM sample was first surface-peeled from the demonstrated membrane, embedded in the mold with epoxy resin, and subsequently polymerized at 70° C. The epoxy-fixed samples were then microtome sectioned and imaged by the Tecnai12 BioTwinG2 (FEI company) instrument at 80 kV. Digital images were acquired using a digital camera system (AMT XR-60 CCD). The surface-peeled samples (without epoxy setting) were also characterized by FTIR (Nicolet iS10 FTIR-ATR) and XRD (Bruker AXS D8) using a copper source (λ=1.54 Å). A GO layer (about 300 nm thick) spin-coated on the silicon wafer support was characterized by GIWAXS, which was performed at the X9 beamline in the National Synchrotron Light Source, Brookhaven National Laboratory.

A custom-made pervaporation apparatus was used to evaluate the ethanol dehydration performance of the membranes. The detailed experimental procedure and setup were reported in an earlier publication. (T. Yeh, D. Mahajan, B. S. Hsiao, B. Chu, JRSE, 4, 041406 (2012).

The GO barrier layer was formed by self-assembly of mostly exfoliated GO sheets, with the total layer thickness being controlled from 93 nm to 618 nm.

The casting procedure included vacuum filtration and spin coating. It was determined that the TFNC membrane itself did not contribute toward the separation of ethanol and water, but its unique support structure could enhance the transport of vapor water molecules through the membrane during pervaporation.

Figure 2:
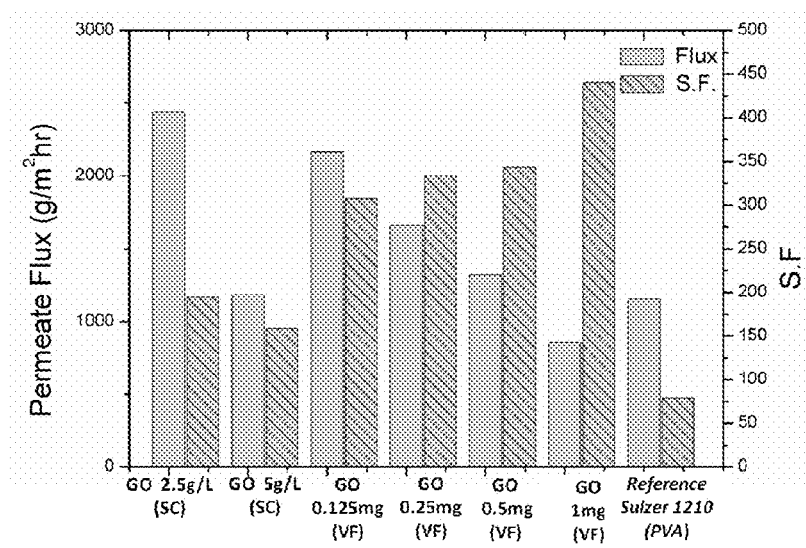
FIG. 2 is a graph comparing pervaporation performance of membranes with various graphene oxide barrier layers of the present disclosure, using an 80 wt % ethanol feed solution at 70° C.

Measurements of the ethanol dehydration efficiency via pervaporation were performed using the GO-based TFNC membranes at different GO layer thicknesses. For example, the 93 nm thick GO membrane showed a permeate flux value of 2.2 (kg/m² hr) and a separation factor of 308 with a feed solution containing 80 wt % ethanol and 20% water at 70° C. (see FIG. 2). The data revealed that all tested GO-based TFNC membranes had a higher separation factor (SF) than the commercial membrane, e.g., the SF value of GO based membranes was at least 159, much higher than 79 from the reference. The better SF performance could be due to the retardation of ethanol transport within the GO barrier layer.

The maximum and minimum water flux values of the tested membranes were 2.4 kg/m² hr and 0.9 kg/m² hr, respectively; these values were significantly better or at least comparable to the flux (1.1 kg/m² hr) from the commercial membrane. It was found that the $GO_1$ and $GO_3$ membranes showed the best overall performance, i.e., the water flux values of 2.4 kg/m² hr and 2.2 kg/m² hr, and SF values of 195 and 308, respectively.

Figure 3:
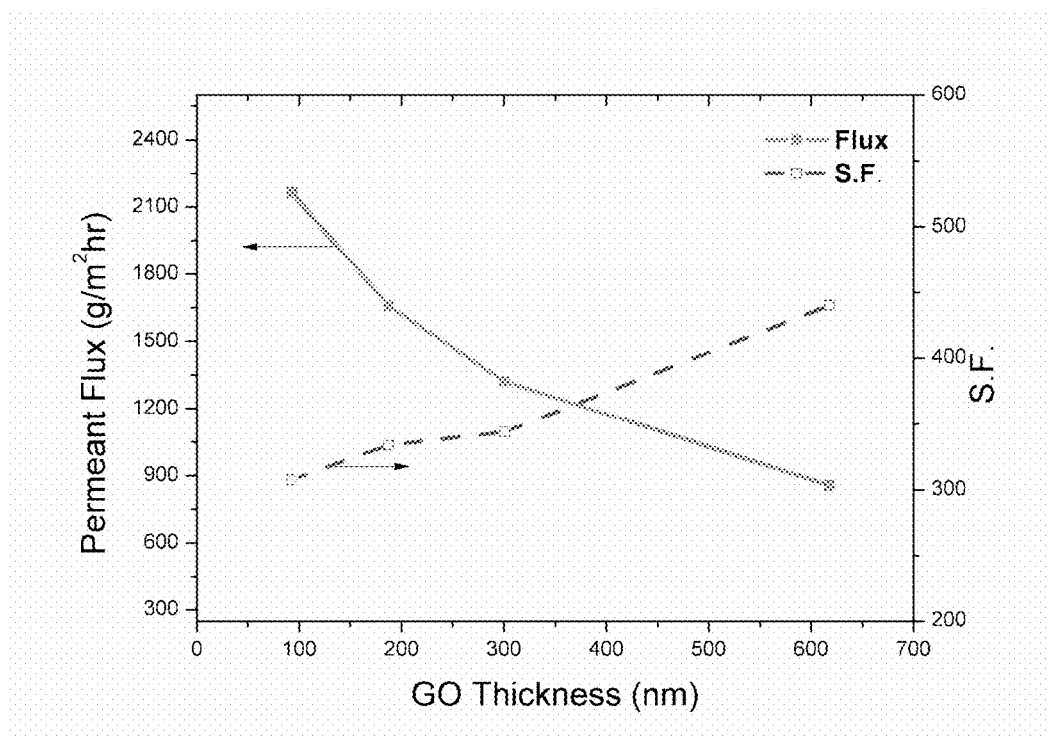
FIG. 3 is a graph depicting the relationship between the permeate flux and separation factor as a function of the thickness of the graphene oxide layer of membranes of the present disclosure, when using 80 wt % ethanol aqueous feed solution at 70° C.

These results were notably superior to those obtained with commercial polymeric membranes for pervaporation (e.g., the water flux increased by a factor of two and the selectivity increased by a factor of four). The GO thickness dependent relationship of the separation factor and the water flux was also observed (see FIG. 3), indicating that further improvements of GO-based TFNC membranes may be obtained by optimizing the barrier layer thickness.

Two possible separate mechanism and morphology models of a GO layer are proposed to explain the phenomenon of the present disclosure. The less-oriented GO layer, including non-exfoliated GO flakes, could have more possible pathways for water (even ethanol) to permeate into the GO stacks from the spacing of intercalating flakes when in comparison with water permeating in an ideally oriented GO layer. On the other hand, the ideal model of orientated GO layer, with mostly exfoliated GO flakes, might reach a more effective separation with the thinner exfoliated GO deposition layer, when compared with the less oriented GO layer. Despite the fact that the current demonstration of GO/TFNC membranes was close to the less oriented model, the results showed the improvements to be superior to the best existing commercial product. Further, the performance could be improved through specific fabrication processes with higher fractions of exfoliated GO flakes and controlled influence on the size and functional groups of GO flakes to the layer morphology.

There are two unique features in GO composite membranes for pervaporation (PV) applications, such as separation of water and ethanol. First, the composite membranes fabricated by using the GO barrier layer can have significantly higher permeation flux and than those conventional polymeric membranes. Second, according to the two proposed models, a GO composite membrane could be further improved to enhance the efficiency of ethanol dehydration through PV, by modifying the surface properties of the GO layer, the dimension of GO flakes, and further reduction of the thickness of the GO layer. The use of exfoliated GO with combined features of surface modification and morphology manipulation provides a new class of pervaporation membranes with simultaneous enhancements of permeation flux and separation factor.

While the above description contains many specific details of methods in accordance with this disclosure, these specific details should not be construed as limitations on the scope of the disclosure, but merely as exemplifications of preferred embodiments thereof. Those skilled in the art will envision many other possible variations that are all within the scope and spirit of the disclosure.

What is claimed is:

1. An article comprising:
    a nanofibrous scaffold comprising fibers having a diameter of from about 1 nm to about 20,000 nm; and
    a barrier layer comprising graphene oxide on at least a portion of a surface of the nanofibrous scaffold,
    wherein the barrier layer has a thickness from about 5 nm to about 5000 nm.

2. The article of claim 1, wherein the nanofibrous scaffold comprises a polymer selected from the group consisting of polyolefins, polysulfones, fluoropolymers, polyesters, polyamides, polycarbonates, polystyrenes, polynitriles, polyacrylates, polyacetates, polyalcohols, polysaccharides, proteins, polyalkylene oxides, polyurethanes, polyureas, polyimines, polyacrylic acids, polymethacrylic acids, polysiloxanes, poly(ester-co-glycol) copolymers, poly(ether-co-amide) copolymers, derivatives thereof and copolymers thereof.

3. The article of claim 1, wherein the nanofibrous scaffold comprises a polymer selected from the group consisting of polyethylene, polypropylene, polyethersulfone, polyvinylidene fluoride, polyethylene terephthalate, polytrimethylene terephthalate, polybutylene terephthalate, nylon 6, nylon 66, nylon 12, polystyrene, polyacrylonitrile, polymethyl methacrylate, polyvinyl acetate, polyvinyl alcohol, chitosan, cellulose, collagen, gelatin, polyethylene oxide, polyethylene glycol, polyvinyl chloride, polyethylene imine, polyvinylpyrrolidone, polydimethylsiloxane, derivatives thereof and copolymers thereof.

4. The article of claim 1, wherein the nanofibrous scaffold has a thickness of from about 1 μm to about 500 μm.

5. The article of claim 1, further comprising an additional barrier layer between the nanofibrous scaffold and the graphene oxide barrier layer, the additional barrier layer formed from a material selected from the group consisting of cellulose nanofibers, chitin nanofibers, and combinations thereof, wherein the additional barrier layer has a thickness from about 0.25 μm to about 2.5 μm.

6. The article of claim 1, further comprising a substrate, wherein the nanofibrous scaffold is applied to at least a portion of the substrate.

7. The article of claim 6, wherein the substrate comprises a polymer selected from the group consisting of polyolefins, polyesters, polyamides, polyurethanes, polysulfones, polyureas, fluorinated polymers, derivatives thereof and copolymers thereof.

8. The article of claim 7, wherein the polymer is selected from the group consisting of polyethylene, polypropylene, polyethylene terephthalate, polytrimethylene terephthalate, polybutylene terephthalate, nylon 6, nylon 66, nylon 12, derivatives thereof, and copolymers thereof, polyetherketones, polystyrene, sulfonated polyetherketones, sulfonated polystyrene, glass, cellulose, derivatives thereof, and copolymers thereof.

9. The article of claim 6, wherein the substrate is selected from the group consisting of polysulfones, cellulose acetates, fluoropolymers, polyamides, polyimides, and combinations thereof, and wherein the substrate has a pore size of from about 5 nm to about 500 nm.

10. A method for purifying an alcohol by pervaporation, the method comprising contacting the alcohol with the article of claim 1.

11. The article of claim 1, wherein the nanofibrous scaffold further comprises a zeolite.

12. The article of claim 1, wherein the graphene oxide barrier layer further comprises a zeolite.

13. An article comprising:
    a substrate;

a nanofibrous scaffold comprising fibers having a diameter of from about 1 nm to about 20,000 nm applied to a surface of the substrate; and a barrier layer comprising graphene oxide on the nanofibrous scaffold on a surface opposite the surface applied to the substrate, wherein the barrier layer has a thickness from about 5 nm to about 5000 nm.

14. The article of claim 13, wherein the substrate comprises a polymer selected from the group consisting of polyolefins, polyesters, polyamides, polyurethanes, polysulfones, polyureas, fluorinated polymers, derivatives thereof and copolymers thereof.

15. The article of claim 13, wherein the nanofibrous scaffold comprises a polymer selected from the group consisting of polyolefins, polysulfones, fluoropolymers, polyesters, polyamides, polycarbonates, polystyrenes, polynitriles, polyacrylates, polyacetates, polyalcohols, polysaccharides, proteins, polyalkylene oxides, polyurethanes, polyureas, polyimines, polyacrylic acids, polymethacrylic acids, polysiloxanes, poly(ester-co-glycol) copolymers, poly(ether-co-amide) copolymers, derivatives thereof and copolymers thereof.

16. The article of claim 13, wherein the nanofibrous scaffold has a thickness of from about 1 μm to about 500 μm and possesses voids with an effective diameter of from about 10 nm to about 200 μm.

17. The article of claim 13, further comprising an additional barrier layer between the nanofibrous scaffold and the graphene oxide barrier layer, the additional barrier layer formed from a material selected from the group consisting of cellulose nanofibers, chitin nanofibers, and combinations thereof, wherein the additional barrier layer has a thickness from about 0.25 μm to about 2.5 μm.

18. A method for purifying an alcohol by pervaporation, the method comprising contacting the alcohol with the article of claim 13.

19. The article of claim 13, wherein the nanofibrous scaffold further comprises a zeolite.

20. The article of claim 13, wherein the graphene oxide barrier layer further comprises a zeolite.

* * * * *